(12) United States Patent
Sugiura et al.

(10) Patent No.: US 10,823,682 B2
(45) Date of Patent: Nov. 3, 2020

(54) WATER MEASUREMENT APPARATUS

(71) Applicant: SAMSUNG ELECTRONICS CO., LTD., Suwon-si (KR)

(72) Inventors: Takamasa Sugiura, Yokohama (JP); Fumitaka Moroishi, Yokohama (JP); Masato Kajinami, Yokohama (JP)

(73) Assignee: Samsung Electronics Co., Ltd., Suwon-si (KR)

(*) Notice: Subject to any disclaimer, the term of this patent is extended or adjusted under 35 U.S.C. 154(b) by 0 days.

(21) Appl. No.: 16/583,434

(22) Filed: Sep. 26, 2019

(65) Prior Publication Data

US 2020/0217805 A1 Jul. 9, 2020

(30) Foreign Application Priority Data

Jan. 8, 2019 (JP) .................... 2019-001236

(51) Int. Cl.
*H01L 21/78* (2006.01)
*G01N 21/95* (2006.01)
(Continued)

(52) U.S. Cl.
CPC ..... *G01N 21/9505* (2013.01); *G01N 21/6456* (2013.01); *G01N 21/6489* (2013.01); *G01N 21/8806* (2013.01); *G06T 7/0004* (2013.01); *H01L 21/67092* (2013.01); *H01L 21/67288* (2013.01); *H01L 21/68707* (2013.01); *H04N 5/2256* (2013.01); *H04N 5/2353* (2013.01);
(Continued)

(58) Field of Classification Search
CPC ........... G01N 21/9505; G01N 21/6456; G01N 21/6489; G01N 21/8806; G01N 2021/8835; G01N 2021/8845; G01N 2201/12; G06T 7/0004; G06T 2207/10048; G06T 2207/10144; G06T 2207/10152; G06T 2207/30148; H01L 21/67092; H01L 21/67288; H01L 21/68707; H04N 5/2256; H04N 5/2353
See application file for complete search history.

(56) References Cited

U.S. PATENT DOCUMENTS

2013/0043405 A1* 2/2013 Maxwell ............ G01N 21/6489
250/459.1
2019/0157151 A1* 5/2019 Sekiya .................... H01L 21/78

FOREIGN PATENT DOCUMENTS

CN 1648632 A 8/2005
WO WO-2004072585 A2 * 8/2004 ......... G01N 21/9501

* cited by examiner

*Primary Examiner* — Thai Q Tran
*Assistant Examiner* — Jose M Mesa
(74) *Attorney, Agent, or Firm* — Lee IP Law, PC

(57) ABSTRACT

A wafer measurement apparatus for measuring a bonding strength of a bonded wafer includes a wafer holder to hold a bonded wafer into which a blade is inserted and where a crack occurs, a lighting assembly including a light source, a light source controller to select the light source of the lighting assembly for detection of the crack reflected in the bonded wafer, on photographing conditions, a photographing assembly to photograph the bonded wafer by using the photographing conditions corresponding to a wavelength of the light source, on sensitivity of the wavelength of the light source, and a calculator to select one photographing condition, transmit the selected photographing condition, and calculate bonding strength, on a crack distance from a blade edge, extracted from an image of the bonded wafer, to a crack edge.

20 Claims, 4 Drawing Sheets

(51) Int. Cl.
  *H01L 21/67* (2006.01)
  *G01N 21/64* (2006.01)
  *G01N 21/88* (2006.01)
  *H04N 5/235* (2006.01)
  *H04N 5/225* (2006.01)
  *G06T 7/00* (2017.01)
  *H01L 21/687* (2006.01)

(52) U.S. Cl.
  CPC ............... *G01N 2021/8835* (2013.01); *G01N 2021/8845* (2013.01); *G01N 2201/12* (2013.01); *G06T 2207/10048* (2013.01); *G06T 2207/10144* (2013.01); *G06T 2207/10152* (2013.01); *G06T 2207/30148* (2013.01)

FIG. 3
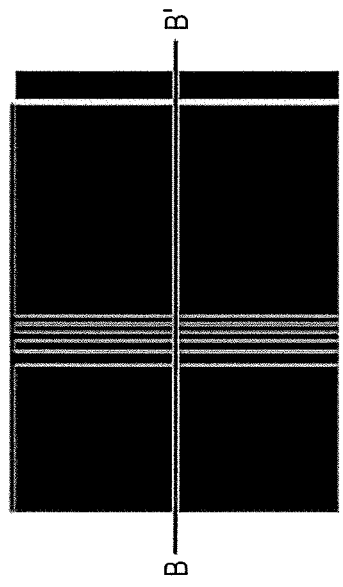
(a) INPUT IMAGE CORRESPONDING TO FIG. 2(a)
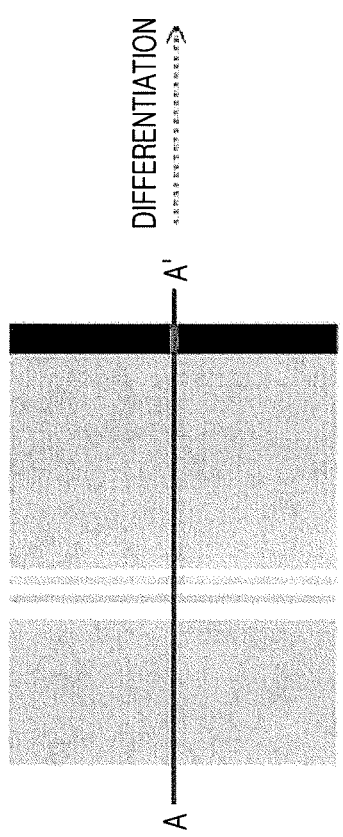
(c) GRAY VALUE PROFILE IN LINE A-A'
DIFFERENTIATION
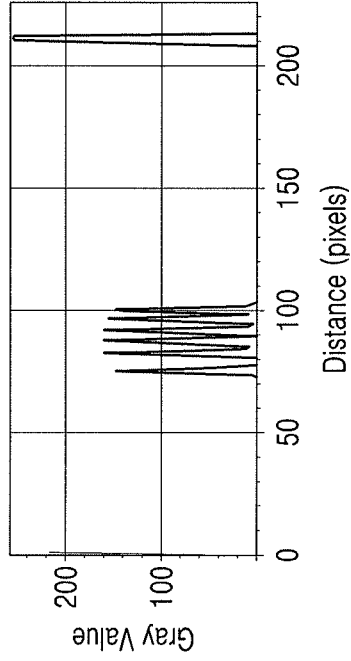
(b) GRADIENT STRENGTH IMAGE CORRESPONDING TO FIG. 2(e)
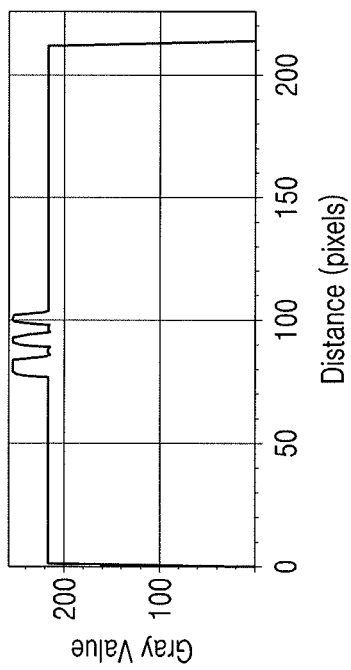
(d) GRAY VALUE PROFILE IN LINE B-B'

WAFER MEASUREMENT APPARATUS

CROSS-REFERENCE TO RELATED APPLICATION

Japanese Patent Application No. 2019-001236, filed on Jan. 8, 2019, in the Japanese Patent Office, and entitled: "Wafer Measurement Apparatus," is incorporated by reference herein in its entirety.

BACKGROUND

1. Field

Embodiments relate to a wafer measurement apparatus.

2. Description of the Related Art

To highly integrate a semiconductor device, a three-dimensional stacking structure may be used for the semiconductor device. For example, a bonding surface between two wafers (semiconductor wafers) may be activated by plasma, and the two wafers may be bonded to each other by pressing center portions of the wafers in a state where the wafers are respectively disposed in a lower portion and an upper portion.

SUMMARY

Embodiments are directed to a wafer measurement apparatus, including a wafer holder to hold a bonded wafer into which a blade is inserted and where a crack occurs, a lighting assembly including a light source having at least two wavelengths, a light source controller to select the light source of the lighting assembly used for detection of the crack reflected in the bonded wafer, based on photographing conditions, a photographing assembly to photograph the bonded wafer by using the photographing conditions corresponding to a wavelength of the light source, based on sensitivity of the wavelength of the light source, and a calculator to select one photographing condition from among the photographing conditions, transmit the selected photographing condition, and calculate bonding strength, based on a crack distance from a blade edge, extracted from an image of the bonded wafer, to a crack edge.

Embodiments are also directed to a wafer measurement apparatus, including a stage, the stage to receive a bonded wafer thereon, a blade, the blade being controlled so as to move in a direction parallel to an upper surface of the stage so as to contact an edge of the bonded wafer and be inserted between a first wafer and a second wafer of the bonded wafer, a light that provides at least two different infrared (IR) wavelengths, the light being located relative to the bonded wafer so as to illuminate a first surface of the bonded wafer such that IR light is transmitted through the first and second wafers to exit a second surface of the bonded wafer, and an IR sensor receiving the IR light transmitted through the first and second wafers via a second surface of the bonded wafer. During a first period, the light provides a first IR wavelength of the at least two different IR wavelengths to the bonded wafer while the IR sensor receives the light of the first IR wavelength, and, during a second period that does not overlap the first period, the light provides a second IR wavelength of the at least two different IR wavelengths to the bonded wafer while the IR sensor receives the light of the second IR wavelength.

Embodiments are also directed to a wafer measurement apparatus, including a stage, the stage to receive a bonded wafer thereon, a blade, the blade being controlled so as to move in a direction parallel to an upper surface of the stage so as to contact an edge of the bonded wafer and be inserted between a first wafer and a second wafer of the bonded wafer, a light that provides at least two different infrared (IR) wavelengths, the light being located relative to the bonded wafer so as to illuminate a first surface of the bonded wafer such that IR light is transmitted through the first and second wafers to exit a second surface of the bonded wafer, an IR sensor receiving the IR light transmitted through the first and second wafers via a second surface of the bonded wafer, and a lighting controller that selectively activates light emitting diodes that emit one among the first through fourth IR wavelengths, which are different from each other, the activated light emitting diodes providing IR light that is illuminated on the first surface of the bonded wafer.

BRIEF DESCRIPTION OF THE DRAWINGS

Features will become apparent to those of skill in the art by describing in detail example embodiments with reference to the attached drawings in which:

FIG. 3 illustrates a schematic diagram for describing image data illustrated in (e) of FIG. 2.

DETAILED DESCRIPTION

Hereinafter, a wafer measurement apparatus according to an example embodiment will be described with reference to the accompanying drawings.

Figure 1:
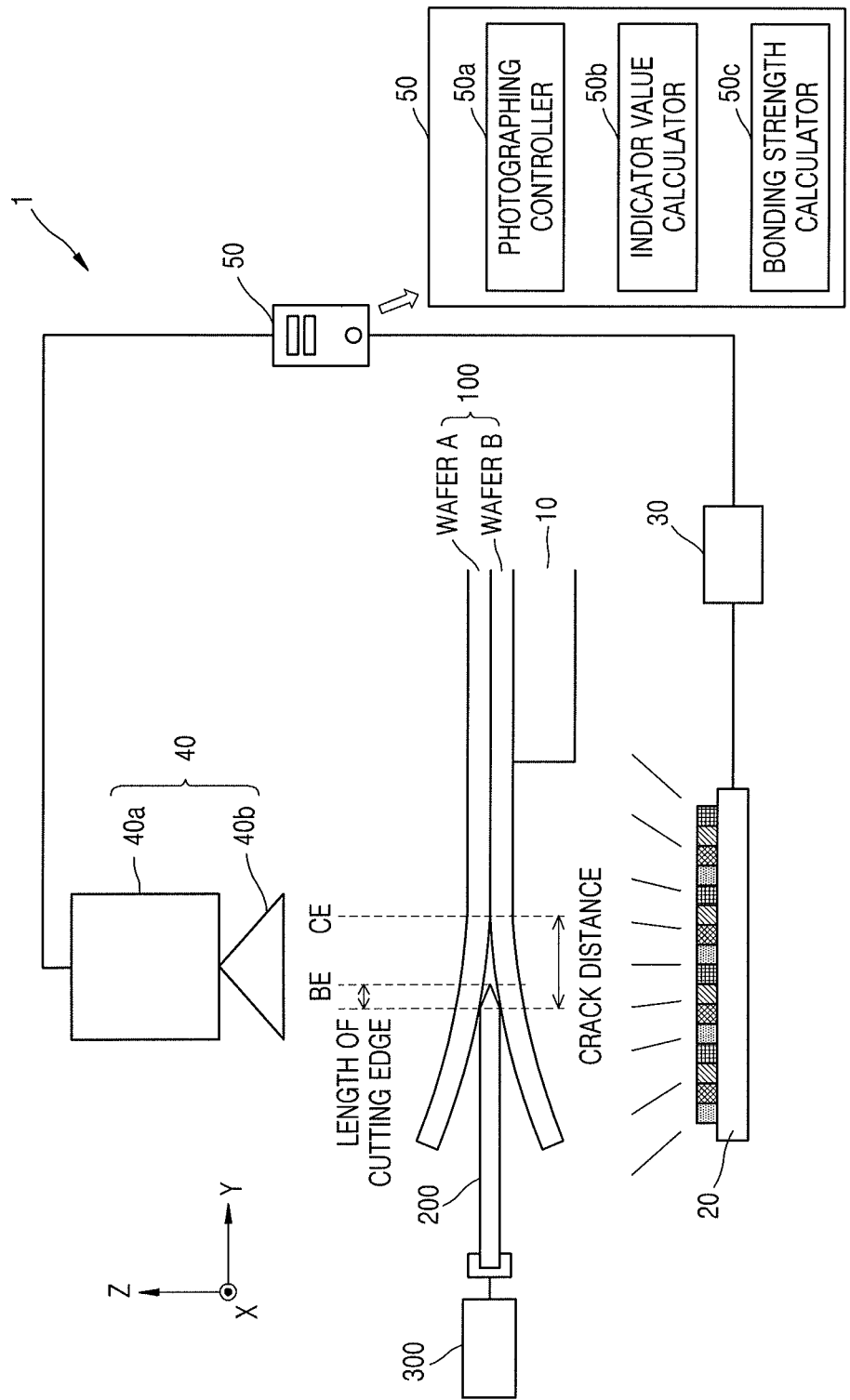
FIG. 1 illustrates a block diagram of a wafer measurement apparatus according to an example embodiment.

FIG. 1 is a block diagram of a wafer measurement apparatus according to an example embodiment.

In detail, the wafer measurement apparatus 1 illustrated in FIG. 1 may include a stage 10 (or a wafer holder), a lighting assembly 20, a lighting controller 30 (or a light adjuster), a photographing assembly (or imager) 40, and a calculator 50.

The stage 10 may hold a bonded wafer 100. The stage 10 may hold only a portion, instead of a whole surface, of the bonded wafer 100 so as not to affect debonding of the bonded wafer 100, and thus, a contact point (or a contact portion) and a debonding portion of the bonded wafer 100 may not coincide. For example, a debonding portion of the bonded wafer 100 may be offset laterally beyond a peripheral edge of the stage 10. The stage 10 may be of various types capable of holding the bonded wafer 100, and may have various shapes, instruments, and materials. For example, the stage 10 may be a type where the bonded wafer is fitted thereinto like a chuck (an electrostatic chuck, a vacuum chuck, etc.) or a vise instrument.

The bonded wafer 100 may include, for example, first and second wafers, for example a wafer A and a wafer B, respectively, which are bonded to each other. A material or a thickness of the wafer A may differ from that of wafer B. In an example embodiment, the bonded wafer 100 may have a circular shape in an XY plane and may have a certain thickness (for example, a sum of thickness of the wafer A and the wafer B) in a Z direction.

A blade 200, as illustrated in FIG. 1, may be inserted into a region between the wafer A and the wafer B of the bonded wafer 100 so as to cause partial debonding of the bonded wafer 100. In FIG. 1, the bonded wafer 100 may be partially debonded in a direction from a small value to a large value of a Y coordinate.

Here, in FIG. 1, an edge, represented by the large value of the Y coordinate, of a debonding surface of the bonded wafer 100 may be illustrated as a crack edge CE. Also, an edge at which the bonded wafer 100 contacts the blade 200 may be illustrated as a blade edge BE.

A motor 300 may move the blade 200 in a wafer insertion direction (that is, a Y direction) of the bonded wafer 100.

The lighting assembly 20 may have a plurality of wavelengths (at least two wavelengths) of a shortwave infrared (IR) wavelength band. For example, the lighting assembly 20 may emit first IR light having a maximum intensity at a first wavelength and second IR light having a maximum intensity at a second wavelength different from the first wavelength. The lighting assembly 20 may include, as a light source, light-emitting diodes (LEDs) having, for example, four wavelengths (for example, 1070 nm, 1200 nm, 1300 nm, and 1450 nm). The lighting assembly 20 may have a configuration where circuits are divided by units of wavelengths and different current values flow based on wavelengths.

The lighting assembly 20, as illustrated in FIG. 1, may be disposed under the stage 10 (that is, a position "Z<0") and may irradiate light of the LED from the wafer B onto the XY plane of the bonded wafer 100. The lighting controller 30 may control a value of a current flowing from the lighting assembly 20 by units of wavelengths, based on a wavelength setting value and a current setting value (that is, a photographing condition or imaging condition) each transmitted by the calculator 50.

The photographing assembly 40 may include a camera 40a and a lens 40b. The camera 40a may include an InGaAs sensor and may have sensitivity corresponding to the shortwave IR wavelength band. A sensor other than an InGaAs that has sensitivity corresponding to the shortwave IR wavelength band may be used in the camera 40a. The lens 40b may transmit light of the shortwave IR wavelength band.

The photographing assembly 40 may photograph the bonded wafer 100, based on a photographing condition (or imaging condition) corresponding to a wavelength of light. The photographing condition may include one or more of an exposure time setting value (an exposure condition) and a gain of the photographing assembly 40. In an embodiment, the photographing condition may include the wavelength setting value, the current setting value (the exposure condition), the exposure time setting value (the exposure condition), and the gain each corresponding to the wavelength of the light.

The calculator 50 may include a photographing controller 50a, an indicator value calculator 50b, and a bonding strength calculator 50c. The calculator 50 may be, for example, a personal computer (PC). The calculator 50 may be connected to the camera 40a according to a communication standard such as GigE or CameraLink and may receive a captured image from the camera 40a. The calculator 50 may be connected to the lighting controller 30 according to a communication standard, such as Ethernet, universal serial bus (USB), or RS-232, and may set a current value flowing based on wavelengths.

The photographing controller 50a may transmit the photographing condition to the photographing assembly 40 and the lighting controller 30 (or a light source controller), and may control the photographing assembly 40 and the lighting controller 30.

The indicator value calculator 50b may calculate an indicator value corresponding to a photographing condition for the crack edge CE. The crack edge CE is the edge of the crack that is farthest from a blade edge BE (the blade edge BE being an edge at which the bonded wafer 100 contacts the blade 200). The indicator value may correspond to a certain number of pixels from the image of the bonded wafer 100 that is captured by the photographing assembly 200.

The indicator value calculated by the indicator value calculator 50b may include a luminance contrast (an indicator value 1) of the crack edge CE, an internal luminance contrast (an indicator value 2) of the bonded wafer 100, and crack detection reproducibility (an indicator value 3) when detecting the crack edge CE. A method of calculating the indicator values 1 to 3 will be described in sequence below.

(1) Indicator Value Calculation Method 1 (Indicator Value 1: Luminance Contrast of a Crack Edge)

A method of calculating the indicator value 1 will be described with reference to FIG. 2.

Figure 2:
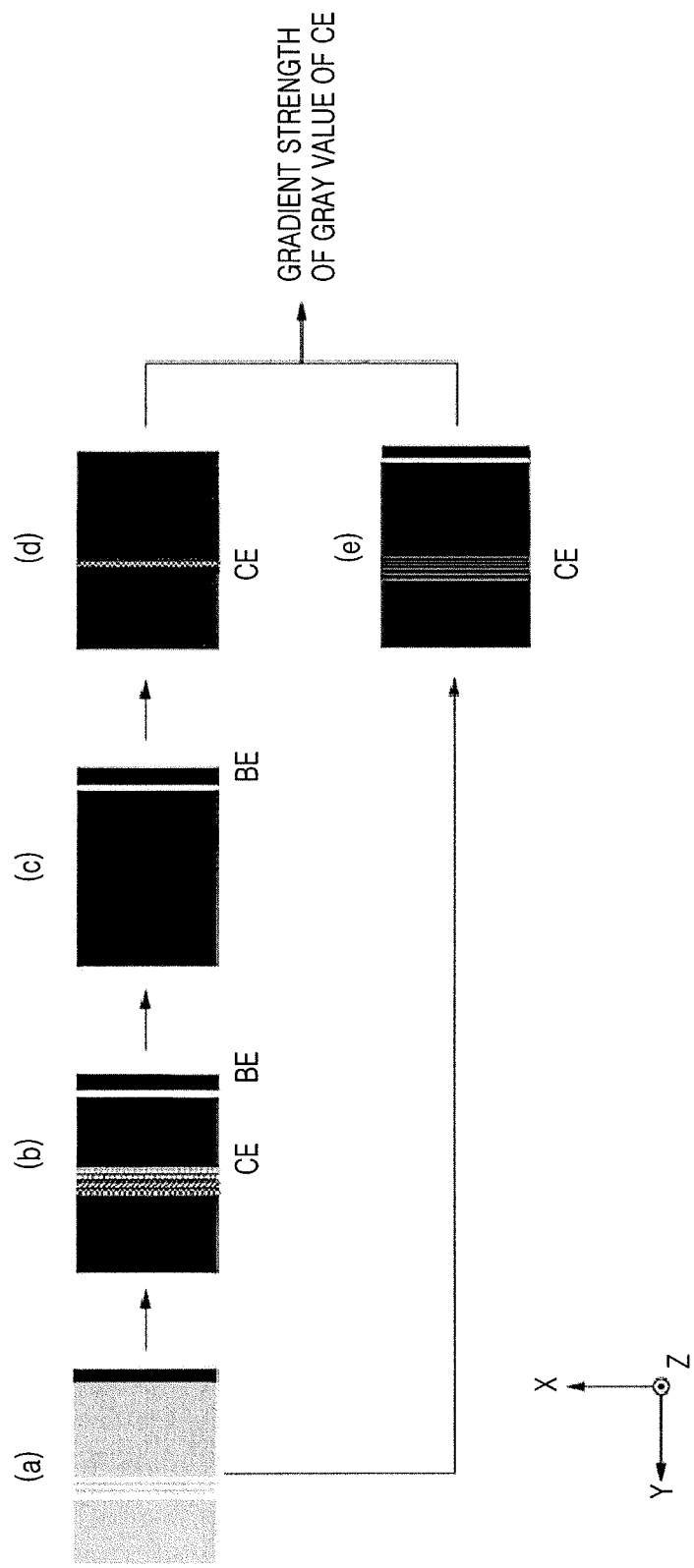
FIG. 2 illustrates a schematic diagram for describing a calculation processing flow in a process of calculating, as an indicator value, a luminance contrast of a crack edge calculated by an indicator value calculator illustrated in FIG. 1.

FIG. 2 is a schematic diagram for describing a calculation processing flow in a process of calculating, as an indicator value, a luminance contrast of the crack edge CE as calculated by the indicator value calculator 50b illustrated in FIG. 1.

In FIG. 2, (a) illustrates an input image that is input from the photographing assembly 40 to the indicator value calculator 50b, and (b) illustrates image data that is obtained through labeling (coloring) showing where an edge region (corresponding generally to the crack edge CE) is extracted from the input image of (a).

Also in FIG. 2, (c) illustrates data for a blade edge BE region (representing a region where the blade edge BE is detected from the image data), and (d) illustrates crack edge CE region data representing a region where the crack edge CE is detected from the image data.

Also in FIG. 2, (e) illustrates image data that represents a gradient strength of a gray value from the input image.

Referring to (a) through (e) in FIG. 2, in the present example method of calculating the indicator value 1, the indicator calculator 50b may extract an edge pixel where a variation in brightness (luminance) is large from the input image of (a) (for example, using a Canny technique or a Canny edge detection technique).

The indicator calculator 50a and may label each of the edge regions CE and BE for a pixel group (for example, where adjacent edge pixels are connected to one another is an edge region). For example, in (b) image data obtained through coloring based on different colors may be used for each label. Respective ones of the edge regions may include the crack edge CE or the blade edge BE.

Subsequently, for (c), the indicator value calculator 50b may extract the blade edge BE from the image data of (b) and may generate the blade edge (BE) region data illustrated in (c). For example, the input image from (b) may be binarized (processed as two values) by using a threshold processing technique, and an edge region in a region where luminance is low may be labeled as the blade edge BE. The threshold value may be a fixed value, a value set by a user, or a value calculated by a determination analysis technique.

Also, for (d), the indicator value calculator 50b may extract the crack edge CE from the image data illustrated in (b) and may generate crack edge CE region data illustrated in (d). In (d), an edge region that is farthest from the blade edge BE and has a certain number of pixels may be labeled as the crack edge CE.

In another example embodiment, a crack edge detection method may include having a user set coordinates of a crack by following a crack with a mouse device or the like, and the user may set a region of interest (ROI) to surround only a crack and a flat portion of the bonded wafer 100, whereby blade detection or labeling may be omitted. Also, the crack may be detected by a discriminator that learns data where the crack is previously set by deep learning or the like.

For (e) of FIG. 2, the indicator value calculator 50b may generate the image data illustrated in (e), representing a gradient strength (contrast) of a gray value from the input image illustrated in (a).

With further reference to (e) of FIG. 2, the image data illustrated in (e) will be described with reference to FIG. 3.

FIG. 3 is a schematic diagram for describing the image data illustrated in (e) of FIG. 2.

In FIG. 3, (a) illustrates an input image corresponding to (a) of FIG. 2, and (b) of FIG. 3 illustrates an image of gradient strength corresponding to (e) of FIG. 2.

Also in FIG. 3, (c) illustrates a gray value profile in line A-A' of (a) of FIG. 3, and (d) illustrates a gray value profile in line B-B' of (b) of FIG. 3.

In (c) and (d) of FIG. 3, the lateral (horizontal) axis represents a distance (pixels), and the longitudinal (vertical) axis represents a gray value (values of 0 to 255 (including 0 corresponding to black, an intermediate value corresponding to gray, and 255 corresponding to white) provided in the line A-A' or the line B-B'.

Referring to the image of a gradient strength in (b) of FIG. 3, pixels where a brightness variation of an input image (illustrated in (c) of FIG. 3) is large may correspond to an image (that is, an image, in which the blade edge BE is bright and the crack edge CE is slightly dark, that has a gray value corresponding to white or an intermediate value) that is bright and where a gradient is large.

Moreover, in the image of the gradient strength of (b) of FIG. 3, a pixel of a flat portion (a portion where a gray value does not vary) illustrated in (c) of FIG. 3 may correspond to an image (that is, an image having a gray value corresponding to black) that is dark.

That is, the image (an image of gradient strength corresponding to (e) of FIG. 2) of the gradient strength illustrated in (b) of FIG. 3 may be an image (an input image corresponding to (a) of FIG. 2) where a gray value variation of the input image illustrated in (a) of FIG. 3 is represented as light and shade.

Referring again to FIG. 2, the indicator value calculator 50b may calculate a gradient strength of a gray value, included in a crack edge CE region, as the indicator value 1 on the basis of (d) and (e) of FIG. 2.

In a case where a gray value is higher than a certain value or there are a certain number of more of pixels, the case may be excluded from an indicator value calculation target. A case where an image is too bright or too dark may be unsuitable for a test, and thus, may be excluded from an indicator value calculation target. Also, in detecting the crack edge CE, a case where there is no label including a certain number or more of pixels may also be excluded from an indicator value calculation target. Even in a case where an edge is extracted regardless of the crack edge CE, a case where only noise or dust is extracted may also be excluded from an indicator value calculation target.

(2) Indicator Value Calculation Method 2 (Indicator Value 2: Internal Contrast of the Bonded Wafer 100)

A method of calculating the indicator value 2 will now be described.

An internal luminance contrast of the bonded wafer 100 may be calculated as the indicator value 2. In extracting an internal region of the bonded wafer 100, a wafer region may be calculated from a feature where a background is bright, a blade is dark, and the bonded wafer 100 has intermediate luminance. The calculation may include dividing a region according to a threshold value processing technique, a K-means algorithm, or a mean-shift algorithm.

In addition, the user may set the wafer region by limiting a boundary of the bonded wafer 100. In a case where there is no factor causing a variation of contrast except for an observation target crack (such as contamination, a crack occurring before inserting a blade, or a void), then an indicator value may be calculated by comparing the indicator value 2 with the indicator value 1.

(3) Indicator Value Calculation Method 3 (Indicator Value 3: Crack Detection Reproducibility)

A method of calculating the indicator value 3 will now be described.

Photographing may be performed under one condition (a wavelength and a current) a plurality of times, and the crack edge CE may be calculated identically to the indicator value calculation method 1.

A non-uniformity of the crack edge CE may be calculated as the indicator value 3 in an image that is obtained through the photographing performed a plurality of times. For example, the non-uniformity may be calculated as a standard deviation of coordinates of the crack edge CE or a difference (maximum value-minimum value) between the maximum value and the minimum value. In another example, a non-uniformity (a standard deviation of coordinates or a difference (maximum value-minimum value) between the maximum value and the minimum value) of a distance from the crack edge CE to the blade edge BE may be calculated as the indicator value 3.

A case where a recommendation indicator value 3 is small may correspond to a case where the crack detection reproducibility is high. A case where the recommendation indicator value 3 is large may correspond to a case where the crack detection reproducibility is low. That is, a level of the indicator value 3 may indicate that the crack detection reproducibility is high or low.

In an example embodiment, the indicator value calculator 50b may calculate an indicator value, determined as an indicator value which is a peak value, from among the calculated indicator values.

In detail, in a process where the photographing controller 50a transmits the photographing condition to the lighting controller 30 (or the light source controller) and the photographing assembly 40 to control the lighting controller 30 and the photographing assembly 40, the photographing controller 50a may fix a wavelength setting value and an exposure time setting value, and may control the lighting controller 30 based on a current value loop which varies a plurality of current setting values.

The photographing controller 50a may transmit a current setting value on the basis of the current value loop, the photographing assembly 40 may perform photographing, and the indicator value calculator 50b may calculate an indicator value (one of the indicator values 1 to 3) (an operation performed in operation S6 described below with reference to FIG. 4).

The indicator value calculator 50b may calculate an indicator value corresponding to each of the plurality of current setting values (that is, may end a current loop), and then may determine whether there is a peak of the indicator value (an operation performed in operation S7 described below with reference to FIG. 4).

Here, that there is a peak may denote that a graph where the lateral axis represents a current value and the longitudinal axis represents an indicator value has a convex shape (a case corresponding to the indicator values 1 and 2) or a convex shape (a case corresponding to the indicator value 3). A case where there is no peak may denote a case where only a flat portion increases and decreases simply, or a case that is excluded from an indicator value calculation target in all current values.

Here, the indicator value calculator 50b may determine whether a best indicator value (a recommendation indicator value) is within a luminance variation range based on a variation of a current setting value in a state where a wavelength setting value is fixed or whether a variation of luminance is further needed.

Moreover, in a case where there is no peak, the photographing controller 50a may proceed to an exposure time loop that varies an exposure time (an exposure condition) of the photographing assembly 40 in a state where the wavelength setting value and the current setting value are fixed (an operation performed in operation S8 which will be described below with reference to FIG. 4).

In a case where there is a peak, when photographing using all wavelength setting values does not end, the photographing controller 50a may vary a wavelength setting value to fix another wavelength setting value and may proceed to a wavelength loop and a current loop, which vary the current setting value. In another implementation, when a current loop corresponding to all wavelength setting values ends, the indicator value calculator 50b may perform an operation of selecting an indicator value from among a recommendation indicator value and indicator values (an operation performed in operation S11 described below with reference to FIG. 4).

Moreover, the photographing assembly 50a may transmit a photographing condition (which corresponds to the selected indicator value) to the lighting controller 30 (or the light source controller), and the photographing assembly 40 and may allow the photographing assembly 40 to photograph the bonded wafer 100 (an operation performed in operation S12 described below with reference to FIG. 4).

The bonding strength calculator 50c may calculate bonding strength based on a crack distance from the blade edge BE (extracted from the image of the bonded wafer 100 captured based on the photographing condition corresponding to the selected indicator value) to the crack edge CE (an operation performed in operation S13 described below with reference to FIG. 4).

Here, the indicator value calculator 50b may extract a blade region by using, for example, the same method as the indicator value calculation method 1. Also, the indicator value calculator 50b may perform a Hough transform on an edge in a blade region to calculate a straight line, and may set the straight line as a blade line (that is, the blade edge BE). Also, by using the same method as the indicator value calculation method 1, the indicator value calculator 50b may calculate the crack edge CE and may set a distance corresponding to a sum of a length of a cutting edge and a distance from the blade edge BE to the crack edge CE as a crack distance. Also, the indicator value calculator 50b may calculate bonding strength from the crack distance, a thickness of the bonded wafer 100, a thickness of the blade 200, and Young's modulus.

Hereinafter, calculation of bonding strength by the wafer measurement apparatus 1 will be described with reference to FIG. 4.

Figure 4:
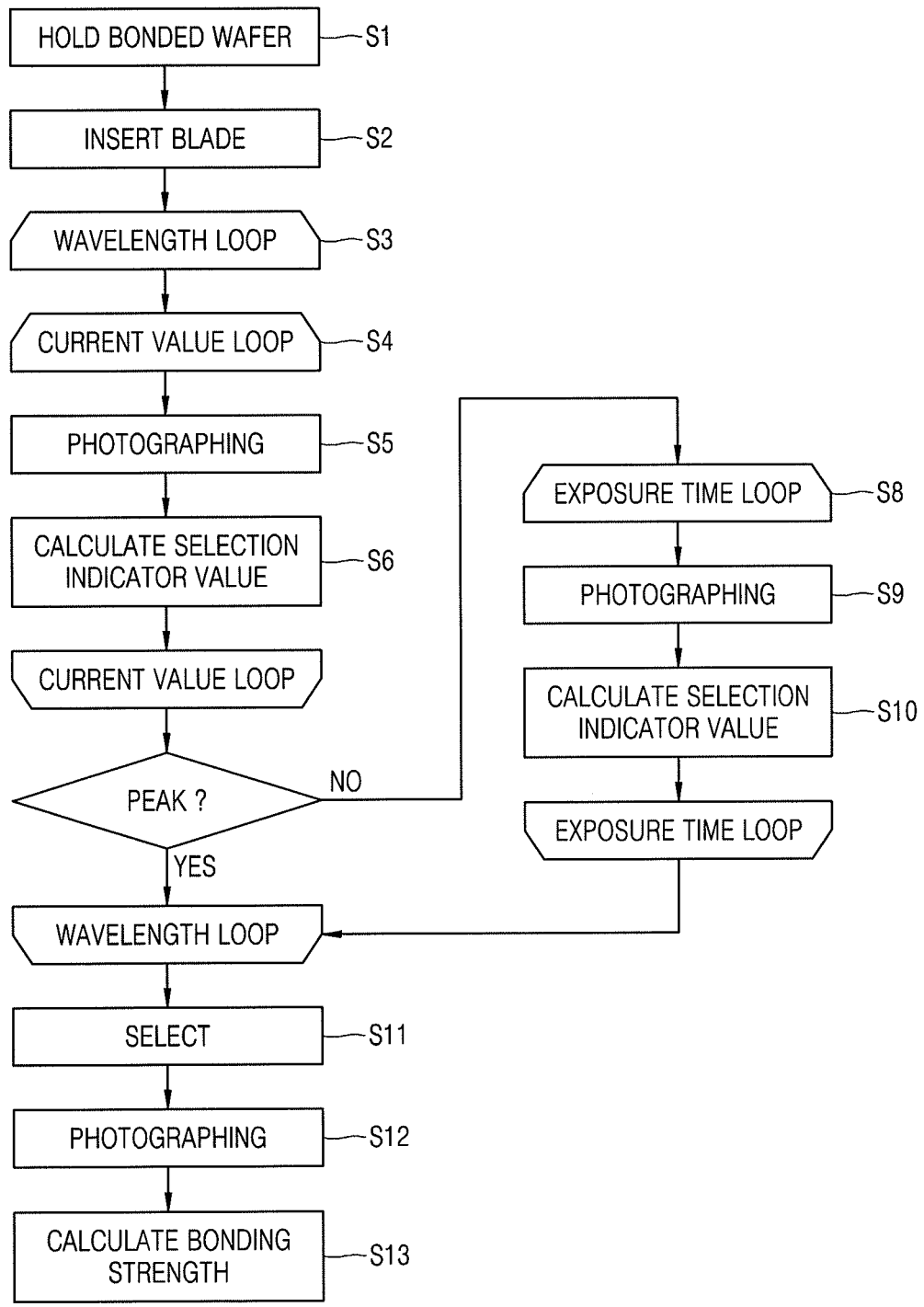
FIG. 4 illustrates a flowchart for an operation performed in a process where the wafer measurement apparatus according to an example embodiment calculates bonding strength.

FIG. 4 is a flowchart illustrating an operation performed in a process where the wafer measurement apparatus 1 according to an example embodiment calculates bonding strength.

Referring to FIG. 4, the stage 10 may hold the bonded wafer 100 in operation S1.

Subsequently, insertion of the blade 200 may be performed in operation S2. In detail, the wafer measurement apparatus 1 may control the motor 300 to move the blade 200 in a wafer insertion direction (the Y direction illustrated in FIG. 1) so as to insert the blade 200 into the bonded wafer 100 and debond a portion of the bonded wafer 100. A case where the bonded wafer 100 is completely debonded or the motor 300 is unable to insert the blade 200 into the bonded wafer 100 (for example, due to a high bonding strength) may be excluded from a bonding strength test target.

The wafer measurement apparatus 1 may start a wavelength loop in operation S3. The wafer measurement apparatus 1 may perform photographing in various wavelengths in the wavelength loop. Here, the photographing controller 30a may control four wavelengths (for example, 1070 nm, 1200 nm, 1300 nm, and 1450 nm) as a wavelength setting value.

In detail, the photographing controller 50a may transmit the wavelength setting value (included in a photographing condition) to the lighting controller 30. The lighting controller 30 may allow the lighting assembly 20, where an LED having a wavelength corresponding to the wavelength setting value is used as a light source, to irradiate light having a wavelength corresponding to the wavelength setting value onto the bonded wafer 100.

The wafer measurement apparatus 1 may start a current value loop in operation S4. The wafer measurement apparatus 1 may perform photographing in various current values. Here, the photographing controller 50a may control the current setting value from 5 mA, with which an LED is stably turned on, to 100 mA, which is a maximum rated current value of the LED.

In detail, the photographing assembly 50a may transmit the current setting value (included in the photographing condition) to the lighting controller 30. The lighting controller 30 may allow a current, corresponding to each of different current setting values based on wavelength setting values, to the lighting assembly 20 where an LED having a wavelength corresponding to the wavelength setting value fixed in operation S3 is used as a light source, and thus the lighting assembly 20 may irradiate light having a wavelength corresponding to the wavelength setting value fixed in operation S3 onto the bonded wafer 100.

The wafer measurement apparatus 1 may perform photographing in operation S5. In detail, the photographing controller 50a may transmit the wavelength setting value and the current setting value to the lighting controller 30 as the photographing condition and may control the lighting controller 30. The lighting controller 30 may select a light source having a wavelength corresponding to the wavelength setting value on the basis of the wavelength setting value and the current setting value each transmitted thereby, and may irradiate the light onto the bonded wafer 100.

Moreover, the photographing controller 50a may transmit an exposure time having a regulation value to the camera 40a of the photographing assembly 40 as the photographing condition and may control a photographing time. That is, the photographing controller 50a may transmit the photographing condition (for example, the wavelength setting value, the current setting value, and an exposure time setting value) to the lighting controller 30 and the photographing assembly 40 as the photographing condition and may control the lighting controller 30 and the photographing assembly 40, thereby allowing an image of the bonded wafer 100 to be captured.

The wafer measurement apparatus 1 may perform a calculation of a selection indicator value in operation S6. In detail, the indicator value calculator 50b may calculate an indicator value corresponding to the photographing condition (for example, the wavelength setting value, the current setting value, and the exposure time setting value) when photographing the bonded wafer 100 in operation S5 in a case of determining whether there is a below-described peak in the captured image in operation S7. The indicator value may include three indicator values (for example, the indicator values 1 to 3) as described above.

The wafer measurement apparatus 1 may determine whether there is a peak of the selection indicator value in operation S7. In detail, the indicator value calculator 50b may end a current loop, and then may determine whether there is an indicator value (a recommendation indicator value), determined as a peak value among the indicator values which are calculated in operation S6, under the photographing condition (for example, the wavelength setting value, the current setting value, and the exposure time setting value) used in the photographing which is performed in operation S5. Here, the three indicator values (for example, the indicator values 1 to 3) in association with the recommendation indicator value have been described above, and thus, their descriptions are omitted.

When there is no recommendation indicator value (step S7—no), operation S8 may be performed. Otherwise, when there is the recommendation indicator value (step S7—yes), operation S11 may be performed. Here, operation S3 may be performed for setting the photographing condition (for example, the wavelength setting value, the current setting value, and the exposure time setting value), used for photographing of the bonded wafer 100 in operation S5, as a next photographing condition (for example, a wavelength setting value, a current setting value, and an exposure time setting value). Also, that operation S11 is performed may denote that photographing of the bonded wafer 100 is completed by using all photographing conditions (for example, a wavelength setting value, a current setting value, and an exposure time setting value).

When there is no recommendation indicator value (step S7—no), the wafer measurement apparatus 1 may start an exposure time loop in operation S8. The wafer measurement apparatus 1 may perform photographing at various exposure times in a wavelength (a wavelength where the recommendation indicator value is not extracted) used in operation S3 in the exposure time loop. The wafer measurement apparatus 1 may perform photographing at various exposure times. An exposure time variation range may be, for example, a range capable of being set from a specification of the camera 40a.

In detail, the photographing controller 50a may transmit the exposure time setting value (included in the photographing condition) to the camera 40a of the photographing assembly 40. The camera 40a may photograph the bonded wafer 100, based on an exposure time corresponding to the exposure time setting value.

The wafer measurement apparatus 1 may perform photographing in operation S9. In detail, the photographing controller 50a may transmit the exposure time to the camera 40a of the photographing assembly 40 as the photographing condition and may control a photographing time. That is, the photographing controller 50a may transmit the photographing condition (for example, an exposure time setting value and a current setting value corresponding to the wavelength setting value used in operation S4) to the lighting controller 30 and the photographing assembly 40, and may control the lighting controller 30 and the photographing assembly 40 while an image of the bonded wafer 100 is captured.

The wafer measurement apparatus 1 may perform calculation of the selection indicator value in operation S10. In detail, the indicator value calculator 50b may calculate an indicator value corresponding to the photographing condition (for example, the wavelength setting value, the current setting value, and the exposure time setting value) when photographing the bonded wafer 100 in operation S9 in a case of performing a below-described selection in operation S11, based on the captured image. The indicator value may include three indicator values (for example, the indicator values 1 to 3) as described above.

The wafer measurement apparatus 1 may perform selection processing in operation S11. In detail, in the indicator values 1 and 2, the indicator value calculator 50b may select an indicator value, which is the maximum, from among the indicator value, which is calculated in steps S6 and S10, and the recommendation indicator value, which is calculated in operation S7. In the indicator value 3, the indicator value calculator 50b may select an indicator value, which is the minimum, from among the calculated indicator values.

Here, that the recommendation indicator value is capable of being calculated in operation S7 may denote that a plurality of calculated indicator values corresponding to the wavelength setting value have a peak in operation S6, and that the recommendation indicator value is incapable of being calculated may denote that the plurality of calculated indicator values corresponding to the wavelength setting value does not have the peak in operation S6.

Therefore, the indicator value, which is calculated in steps S6 and S10 and is used for the selection, may represent an indicator value where a recommendation indicator value corresponding to the wavelength setting value is not calculated. The recommendation indicator value calculated in operation S7 may represent a recommendation indicator value where the recommendation indicator value corresponding to the wavelength setting value is calculated in operation S7.

That is, under all photographing conditions (for example, a wavelength setting value, a current setting value, and an exposure time setting value), there may be five cases including a case where there is a recommendation indicator value corresponding to all (N=4) wavelength setting values, a case where there is a recommendation indicator value corresponding to N=3 number of wavelength setting values, a case where there is a recommendation indicator value corresponding to N=2 number of wavelength setting values, a case where there is a recommendation indicator value corresponding to N=1 number of wavelength setting values, and a case where there is no recommendation indicator value corresponding to a wavelength setting value.

Therefore, in the indicator values 1 and 2, the indicator value calculator 50b may select an indicator value, which is the maximum, from among a plurality of calculated indicator values and the calculated recommendation indicator value. In the indicator value 3, the indicator value calculator 50b may select an indicator value, which is the minimum, from among the plurality of calculated indicator values and the calculated recommendation indicator value. That is, the indicator value calculator 50b may select one indicator value from among an indicator value and a recommendation indicator value, based on a certain condition. Accordingly, in the photographed bonded wafer 100, a best indicator value (one indicator value) may be selected from among the plurality of calculated indicator values and the calculated recommendation indicator value.

The wafer measurement apparatus 1 may perform photographing in operation S12. In detail, the photographing controller 50a may transmit a photographing condition (for example, a wavelength setting value, a current setting value, and an exposure time setting value), representing the indicator value selected by the indicator value calculator 50b in operation S11, to the lighting controller 30 and the photographing assembly 40 and may control the lighting controller 30 and the photographing assembly 40, thereby capturing an image of the bonded wafer 100.

The wafer measurement apparatus 1 may perform calculation in operation S13. In detail, the bonding strength calculator 50c may transmit a photographing condition represented by an indicator value (an indicator value selected based on a certain condition by the indicator value calculator 50b in operation S11) selected by the photographing controller 50a and may calculate bonding strength, based on a distance corresponding to a sum of a length of a cutting edge and a distance from the blade edge BE, extracted from the captured image of the bonded wafer 100, to the crack edge CE.

The wafer measurement apparatus 1 may measure a bonding strength of the bonded wafer 100 at high precision.

In a general method of measuring bonding strength of a bonded wafer, the above-described operations S3 to S11 are not performed (that is, the photographing controller 50a and the indicator value calculator 50b are not provided), and a lighting condition of the same wavelength is used for any bonded wafer. However, when a material of a wafer or a material of a film on the wafer is changed, a reflectance or an absorption rate is changed, and due to this, a crack image is degraded. According to an example embodiment, a measurement may be performed by selecting a wavelength where a contrast (the indicator values 1 and 2) of a crack or a detection performance (the indicator value 3) of the crack is good, and thus, regardless of a material of any wafer, bonding strength may be measured at high precision without reducing a drawing function of the crack.

Hereinabove, the embodiments have been described with reference to the drawings, but the present embodiment is not limited thereto and modifications to the design may be made without departing from the present embodiment.

For example, in an example embodiment, operation S5 may correspond to a current value loop, and operation S8 may correspond to an exposure time loop. Also, operation S4 may correspond to an exposure time loop, and operation S8 may correspond to a current value loop. In this case, in photographing performed in operation S5, a current value may use a regulation value. For example, the regulation value may be referred to as a maximum rated current.

Moreover, for example, the photographing assembly may use a gain value loop. The gain value loop may be replaced by a current value loop or an exposure time loop. In addition to the current value loop or the exposure time loop, the gain value loop may be added. The current value loop, the exposure time loop, and the gain value loop may be loops for adjusting the brightness of an image, and a loop used for adjusting the brightness of an image is not limited. Also, the lighting assembly may include an LED or a halogen lamp each emitting light having a wide band including a short-wave near-infrared wavelength band, and a wavelength may be limited by using a band pass filter.

By way of summation and review, if bonding strength is insufficient, or if the bonded wafers are dropped in transferring (or transporting) or the wafers are debonded from each other in a semiconductor device manufacturing process (such as dicing), the manufacturing yield rate of semiconductor devices may be reduced. In a general bonding strength measurement, a blade may be inserted between two wafers of a bonded wafer, and infrared light, for example, at a single wavelength band, may be directed at the wafer to illuminate a crack between the two wafers. Bonding strength may be calculated from, for example, a distance between the blade and the crack, the thickness of the wafer, the thickness of the blade, and a Young's modulus. However, a light absorption rate varies based on a material of a wafer, and thus, a wavelength or luminance of illumination suitable for observing a crack is adjusted. In a general bonding strength measurement, observation is performed without varying a wavelength and thus insufficient contrast may exist to observe a crack. Thus, a measurement precision of bonding strength may be reduced.

As described above, embodiments may provide a wafer measurement apparatus for measuring a bonding strength of a bonded wafer at high precision.

As described above, a wafer measurement apparatus according to example embodiments may include a calculator that calculates an indicator value corresponding to a photographing condition from an image (an image of a bonded wafer captured based on two or more wavelengths) of a bonded wafer captured by a photographing assembly, and may transmit the photographing condition represented by the indicator value to calculate bonding strength on the basis of a crack distance between a crack edge and a blade edge extracted from the captured image of the bonded wafer. Accordingly, according to example embodiments, a bonding strength of the bonded wafer may be measured at high precision.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A wafer measurement apparatus, comprising:
   a wafer holder to hold a bonded wafer into which a blade is inserted and where a crack occurs;
   a lighting assembly comprising a light source having at least two wavelengths;
   a light source controller to select the light source of the lighting assembly used for detection of the crack reflected in the bonded wafer, based on photographing conditions;
   a photographing assembly to photograph the bonded wafer by using the photographing conditions corresponding to a wavelength of the light source, based on sensitivity of the wavelength of the light source; and a calculator to select one photographing condition from among the photographing conditions, transmit the selected photographing condition, and calculate bonding strength, based on a crack distance from a blade edge, extracted from an image of the bonded wafer, to a crack edge.

2. The wafer measurement apparatus as claimed in claim 1, wherein the photographing assembly is to calculate an indicator value corresponding to the photographing conditions in the image of the bonded wafer, and the one photographing condition is a photographing condition represented by the calculated indicator value.

3. The wafer measurement apparatus as claimed in claim 2, wherein the calculator comprises:
   a photographing controller to transmit the photographing conditions to the photographing assembly and the light source controller to control the photographing assembly and the light source controller;
   an indicator value calculator to calculate an indicator value corresponding to the photographing conditions corresponding to a crack edge which has a certain number or more of pixels and which is farthest from the blade edge which is an edge at which the bonded wafer contacts the blade in the image of the bonded wafer captured by the photographing assembly, calculate a recommendation indicator value determined as an indicator value which is a peak value among one or more indicator values, and select an indicator value from among indicators and the recommendation indicator value, based on a certain condition; and
   a bonding strength calculator to transmit the photographing conditions represented by the selected indicator value to calculate bonding strength on the basis of the crack distance from the blade edge, extracted from the image of the bonded wafer, to the crack edge.

4. The wafer measurement apparatus as claimed in claim 3, wherein the indicator value is a luminance contrast of the crack edge, an internal luminance contrast of the bonded wafer, and crack detection reproducibility when detecting the crack edge.

5. The wafer measurement apparatus as claimed in claim 3, wherein:
   the photographing controller is to transmit the photographing conditions for varying a wavelength and a current value of the lighting assembly to control the lighting assembly and the photographing assembly,
   the indicator value calculator is to calculate a plurality of recommendation indicator values in association with a plurality of wavelengths of the lighting assembly among the photographing conditions,
   when the recommendation indicator value of the calculated plurality of recommendation indictor values is a luminance contrast of the crack edge or an internal luminance contrast of the bonded wafer, the indicator value calculator is to select a largest recommendation indicator value from among the calculated plurality of recommendation indictor values,
   when the recommendation indicator value is crack detection reproducibility when detecting the crack edge, the indicator value calculator is to select a smallest recommendation indicator value from among the calculated plurality of recommendation indicator values corresponding to high and low of the crack detection reproducibility, and
   the photographing controller is to transmit the photographing conditions represented by the selected recommendation indicator value to control the lighting assembly and the photographing assembly.

6. The wafer measurement apparatus as claimed in claim 5, wherein, when the indicator value calculator does not calculate the recommendation indicator value in association with at least one wavelength of the plurality of wavelengths,
   the photographing controller is to transmit a photographing condition, changing an exposure condition of the photographing assembly in association with a wavelength, where the recommendation indicator value is not calculated, of the plurality of wavelengths of the lighting assembly, to control the lighting assembly and the photographing assembly,
   the indicator value calculator is to calculate a plurality of indicator values corresponding to the exposure condition of the photographing assembly among the photographing conditions,
   when the indicator value is a luminance contrast of the crack edge or an internal luminance contrast of the bonded wafer, the indicator value calculator is to select a largest indicator value among the plurality of indicator values and a plurality of indicator values comprising a recommendation indicator value when the recommendation indicator value is capable of being calculated,
   when the indicator value is crack detection reproducibility when detecting the crack edge, the indicator value calculator is to select a smallest indicator value among the plurality of indicator values and a plurality of indicator values comprising a recommendation indicator value when the recommendation indicator value is capable of being calculated, and
   the photographing controller is to transmit the photographing conditions represented by the selected indicator value to control the lighting assembly and the photographing assembly.

7. The wafer measurement apparatus as claimed in claim 1, wherein a light source of the lighting assembly has a wavelength of a shortwave infrared wavelength band.

8. A wafer measurement apparatus, comprising:
   a stage, the stage to receive a bonded wafer thereon;
   a blade, the blade being controlled so as to move in a direction parallel to an upper surface of the stage so as to contact an edge of the bonded wafer and be inserted between a first wafer and a second wafer of the bonded wafer;
   a light that provides at least two different infrared (IR) wavelengths, the light being located relative to the bonded wafer so as to illuminate a first surface of the bonded wafer such that IR light is transmitted through the first and second wafers to exit a second surface of the bonded wafer; and
   an IR sensor receiving the IR light transmitted through the first and second wafers via a second surface of the bonded wafer, wherein:
   during a first period, the light provides a first IR wavelength of the at least two different IR wavelengths to the bonded wafer while the IR sensor receives the light of the first IR wavelength, and
   during a second period that does not overlap the first period, the light provides a second IR wavelength of the at least two different IR wavelengths to the bonded wafer while the IR sensor receives the light of the second IR wavelength.

9. The wafer measurement apparatus as claimed in claim 8, wherein the light alternately provides at least two among first through fourth IR wavelengths using light emitting diodes that emit at 1070 nm, 1200 nm, 1300 nm, and 1450 nm, respectively.

10. The wafer measurement apparatus as claimed in claim 9, further comprising a lighting controller that selectively activates light emitting diodes that emit one among the first through fourth IR wavelengths, the activated light emitting diodes providing IR light that is illuminated on the first surface of the bonded wafer.

11. The wafer measurement apparatus as claimed in claim 10, further comprising a photographing controller that sets a current value applied to the light emitting diodes so as to set a brightness of the IR light that is illuminated on the first surface of the bonded wafer at a respective one of the first through fourth IR wavelengths.

12. The wafer measurement apparatus as claimed in claim 11, wherein, for a given one of the first through fourth IR wavelengths, the IR sensor captures data for a least two different current values applied to light emitting diodes of a same IR wavelength.

13. The wafer measurement apparatus as claimed in claim 8, wherein the IR sensor receives light transmitted through the first and second wafers over an area that includes a first area where the blade is inserted between the first and second wafers, and a second area, contiguous with the first area, where a debonded area and a bonded area of the bonded wafer meet.

14. The wafer measurement apparatus as claimed in claim 8, further comprising a photographing controller, wherein the IR sensor is connected to a process loop whereby first IR data gathered by the IR sensor at a first IR wavelength over a first exposure period is replaced with second IR data gathered at the first IR wavelength at a second exposure period longer than the first exposure period, the process loop being controlled by the photographing controller.

15. The wafer measurement apparatus as claimed in claim 14, wherein the photographing controller also sets a current value applied to light emitting diodes so as to set a brightness of the IR light that is illuminated on the first surface of the bonded wafer.

16. The wafer measurement apparatus as claimed in claim 14, wherein the first IR data and the second IR data each correspond to a plurality of pixels of image data gathered by the IR sensor.

17. The wafer measurement apparatus as claimed in claim 8, further comprising a photographing controller, wherein the photographing controller controls the IR sensor to gather first IR data and second IR data, each corresponding to a plurality of pixels of image data gathered by the IR sensor, the first IR data being gathered during the first period, the second IR data being gathered during the second period.

18. The wafer measurement apparatus as claimed in claim 17, wherein the photographing controller transmits a photographing condition that changes an exposure condition in association with a wavelength.

19. The wafer measurement apparatus as claimed in claim 18, wherein the photographing condition transmitted by the photographing controller represent an indicator value that includes one or more of a luminance contrast of a crack edge generated by the blade, an internal luminance contrast of the bonded wafer, or crack detection reproducibility when detecting the crack edge.

20. A wafer measurement apparatus, comprising:
a stage, the stage to receive a bonded wafer thereon;
a blade, the blade being controlled so as to move in a direction parallel to an upper surface of the stage so as to contact an edge of the bonded wafer and be inserted between a first wafer and a second wafer of the bonded wafer;
a light that provides at least two different infrared (IR) wavelengths, the light being located relative to the bonded wafer so as to illuminate a first surface of the bonded wafer such that IR light is transmitted through the first and second wafers to exit a second surface of the bonded wafer;
an IR sensor receiving the IR light transmitted through the first and second wafers via a second surface of the bonded wafer; and
a lighting controller that selectively activates light emitting diodes that emit one among the first through fourth IR wavelengths, which are different from each other, the activated light emitting diodes providing IR light that is illuminated on the first surface of the bonded wafer.

* * * * *

UNITED STATES PATENT AND TRADEMARK OFFICE
CERTIFICATE OF CORRECTION

PATENT NO.        : 10,823,682 B2  
APPLICATION NO.   : 16/583434  
DATED             : November 3, 2020  
INVENTOR(S)       : Takamasa Sugiura et al.

Page 1 of 1

It is certified that error appears in the above-identified patent and that said Letters Patent is hereby corrected as shown below:

On the Title Page

Item (54) and in the Specification Column 1 Line 1 should be corrected to read:
--WAFER MEASUREMENT APPARATUS--.

Signed and Sealed this  
Fifteenth Day of December, 2020

Andrei Iancu  
*Director of the United States Patent and Trademark Office*